United States Patent [19]

Wurster et al.

[11] Patent Number: 5,060,650
[45] Date of Patent: Oct. 29, 1991

[54] LITHOTRIPTER WITH X-RAY AND ULTRASOUND LOCATION SYSTEMS

[75] Inventors: Helmut Wurster, Oberderdingen; Werner Krauss; Thomas Belikan, both of Knittlingen, all of Fed. Rep. of Germany

[73] Assignee: Richard Wolf GmbH, Knittlinger, Fed. Rep. of Germany

[21] Appl. No.: 494,208

[22] Filed: Mar. 15, 1990

[30] Foreign Application Priority Data

May 17, 1989 [DE] Fed. Rep. of Germany ....... 3916093

[51] Int. Cl.$^5$ ............................................. A61B 17/22
[52] U.S. Cl. ......................... 128/660.03; 128/24 EL
[58] Field of Search ......... 128/24 EL, 660.03, 653 R; 378/147, 198

[56] References Cited

U.S. PATENT DOCUMENTS

| | | | |
|---|---|---|---|
| 4,716,581 | 12/1987 | Barud | 378/198 |
| 4,836,191 | 6/1989 | Noske et al. | 128/24 EL |
| 4,866,752 | 9/1989 | Bock et al. | 378/198 |
| 4,896,673 | 1/1990 | Rose et al. | 128/660.03 |
| 4,913,156 | 4/1990 | Inbar et al. | 128/660.03 |
| 4,936,291 | 6/1990 | Forssmann et al. | 128/660.03 |
| 4,947,830 | 8/1990 | Rattner et al. | 128/660.03 |

FOREIGN PATENT DOCUMENTS

| | | |
|---|---|---|
| 0205878 | 12/1986 | European Pat. Off. ....... 128/24 EL |
| 2722252 | 11/1978 | Fed. Rep. of Germany ... 128/24 EL |
| 3426398 | 3/1986 | Fed. Rep. of Germany . |
| 8528785 | 7/1986 | Fed. Rep. of Germany . |
| 8515656 | 1/1987 | Fed. Rep. of Germany . |
| 8534425 | 6/1987 | Fed. Rep. of Germany . |
| 3704909 | 8/1988 | Fed. Rep. of Germany . |
| 3826709 | 2/1989 | Fed. Rep. of Germany . |

OTHER PUBLICATIONS

Dornier article entitled, "Dornier Nierenlithotripter", (Dornier Kidney Lithotripter: non-invasive kidney stone disintegration).

Primary Examiner—Ruth S. Smith
Attorney, Agent, or Firm—Panitch, Schwarze, Jacobs & Nadel

[57] ABSTRACT

A lithotripter comprises a transducer for generating focussed ultrasonic shock waves, and having an axis, a focus on said axis, the focus being positionable on a concretion or tissue which is to be destroyed, at least one diagnostic X-ray imaging system for locating the concretion of tissue including an X-ray emitter having an axis and an image intensifier, and at least one ultrasonic locating transducer having an axis, the X-ray emitter and the ultrasonic locating transducer being connected to the shock wave transducer in such a way that the axes of the locating systems intersect at said focus, with the axes of the locating systems preferably being offset from the axis of the shock wave transducer.

12 Claims, 6 Drawing Sheets

LITHOTRIPTER WITH X-RAY AND ULTRASOUND LOCATION SYSTEMS

CROSS REFERENCE TO RELATED APPLICATIONS

This application is related to our copending application Ser. Nos. 408,835, filed Sept. 18, 1989, entitled "Lithotripter"; and 574,330, filed Aug. 28, 1990, entitled "Lithotripter Comprising a Locating System".

BACKGROUND OF THE INVENTION

(1) Field of the Invention

This invention relates to a lithotripter having a transducer for generating focussed ultrasonic shock waves and having an axis and a focus, and at least one diagnostic X-ray imaging system for locating a concretion or tissue to be destroyed at the said focus, which system may be arranged on a frame which can be pivoted about an axis in various image planes for locating purposes.

(2) Description of the Prior Art

Examples of known lithotripters in which location of a concretion, e.g., a kidney stone, which is required for every lithotripsy and which precedes the destruction of the concretion by ultrasonic shock waves is carried out with an X-ray system are disclosed in DE-GM 8515656, DE-GM 8528785 and DE-GM 8534425.

For location of this kind at least two planes of irradiation are needed. What are normally used for this purpose are the so-called AP projection and a projection pivoted through 30° from it. Once the concretion to be destroyed has been successfully located, its spatial coordinates are found electronically. Complex electronic and mechanical systems then move the ultrasonic shock wave transducer until its focus lies in the region defined by the spatial co-ordinates which were found. Only then is it possible and medically sensible for ultrasonic shock waves to be applied.

One disadvantage of such known lithotripters is that once the concretion to be destroyed has been located with the X-ray system, the focus of the shock wave transducer must first be moved so that it is positioned on the concretion, if the patient is not to be moved from the position which he/she occupied when the concretion was located. Another disadvantage is that although there are many conditions where ultrasonic location of the concretion is indicated, this type of location is not possible with the known units using X-ray location.

The main object of the present invention is to provide a lithotripter in which X-ray location and ultrasonic location of the concretion to be destroyed are possible simultaneously or independantly of each other with no change in the position of the patient. It must be possible for real-time X-ray location to be carried out both during the shock wave application and during the adjustment of the locating systems.

SUMMARY OF THE INVENTION

To this end, the present invention consists in a lithotripter comprising a transducer for generating ultrasonic shock waves, and having an axis and a focus on said axis, at least one X-ray imaging system for locating a concretion or tissue to be destroyed by said shock waves at said focus, and having an axis, and at least one ultrasonic locating transducer, said location systems preferably being arranged on a frame which is pivotable about an axis in various image planes for locating purposes, wherein the locating systems are connected to the shock wave generating transducer in such a way that the axis of the shock wave generating transducer and the axes of the locating systems intersect at the focus of the shock wave generating transducer, the axes of said locating systems preferably being offset from the axis of the shock wave generating transducer.

It is advantageous to position the X-ray emitter of the X-ray imaging system so that it is offset from the axis of the shock wave transducer because the pivoting movement of the X-ray system from the position where the axis of the shock wave transducer is vertically aligned can be carried out through an angle which is divided about the axis of the X-ray emitter. If for example the axis of the X-ray emitter is offset 15° from the axis of the shock wave transducer, the X-ray system only needs to be pivoted through ±15° from a rest or datum position of axis of the X-ray emitter to produce the AP projection mentioned above and the 30° projection. With the unit comprising the X-ray emitter, ultrasonic locating transducer and shock wave transducer in a so-called undertable or underpatient arrangement, the divided angle of pivot provides the unit with a longer travel in the vertical direction than would be possible if the pivoting took place through an undivided angle, because in the latter case the unit would, by contrast, strike against the bottom face of a treatment table for the patient.

In an advantageous refinement, the isocenter for the pivoting movement of the X-ray system and its frame is the focus, an imaginary linear extension of the pivot axis of the frame intersecting the focus in any pivoted position. This makes it unnecessary for the unit comprising the X-ray emitter, ultrasonic locating transducer and shock wave transducer to be moved, along linear axes, because the focus of the shock wave transducer always remains positioned on the concretion or tissue when the X-ray system is pivoted to locate the latter.

Also, the shock wave transducer may be a piezoelectric or magnetostrictive transducer or an eddy-current transducer with the transducer being designed to be self-focussing or to focus through an acoustic lens or to have a reflector system. As well as this, it is, however, perfectly possible for a shock wave transducer with a spark-gap to be used. Preferably, the shock wave transducer is of part-spherical shape so that the ultrasonic shock waves emitted by it are automatically brought to a focus.

The ultrasonic locating transducers may, for example, be B-scanners of known type.

Because the shock wave transducer is fitted with the above mentioned locating systems, the concretion or tissue may be located both by means of the X-ray system and by means of the ultrasonic locating transducer. It is equally possible for the process of destroying the concretion or tissue to be observed in real time as the shock waves are being applied with either of the two locating systems or with both simultaneously, as desired.

In a preferred embodiment of the invention, the ultrasonic locating transducer is advantageously positioned as a mirror image of the X-ray emitter about the shock wave transducer axis. If the X-ray emitter is offset 15° from the axis of the shock wave transducer the ultrasonic locating transducer will likewise be offset 15° from this same axis in a position diametrically opposed to the X-ray emitter. This arrangement ensures that the locating transducer does not project at all, or only projects to a small extent, into the X-ray beam such as a cone of X-rays, leaving the X-ray emitter.

If, in the case of the lithotripter according to the invention, the shock waves generated by the shock wave transducer are transmitted to the patient's body via a liquid acting as a coupling medium, it may be advantageous for better or improved X-ray location for the X-ray emitter to be provided with a gas-filled tube which is sealed or closed off from its surroundings, i.e., the ambient medium, and whose cross-section matches the cross-section of the X-ray beam emitted by the X-ray emitter for location purposes. This counteracts any attenuation of the X-ray radiation in the coupling medium because the tube removes the coupling medium from the path taken by the X-ray beam from the X-ray emitter to the patient's body.

Moreover, it is advantageous for the tube to project almost exactly as far into the shock wave transducer as the ultrasonic locating transducer.

In order to achieve an optimum relationship between an X-ray image of good quality on the one hand and the least possible masking of the shock wave field on the other hand, the gas-filled tube is preferably movable along the axis of the X-ray emitter.

Another advantageous refinement of this embodiment of lithotripter can be obtained by closing off the free end of the tube adjacent the focus with a balloon which can be filled with gas. In this way it is possible completely to expel any coupling medium which may possibly still be present between the end of the tube and the body of the patient in the said embodiment. For the purpose of optimum X-ray location, the balloon can be pumped up with gas via a suitable pipe, using a pressurising pump. Once the location has taken place, the balloon can then be evacuated with a vacuum pump so that the coupling medium is again able properly to couple the shock waves from the shock wave transducer to the patient's body during therapy.

To keep the pressure in the coupling medium constant while the balloon is being inflated, a volume of the coupling fluid which is constantly equal to the volume of the balloon can be conveyed to an equalising system which is known per se. While the gas is being withdrawn from the balloon by the vacuum pump, the coupling liquid which was previously transferred to the equalising system can be returned to the main body of coupling medium.

An advantageous facility for positioning the focus on the concretion or the tissue to be destroyed is provided if the treatment table on which the patient rests is movable along the X,Y and Z axes, with the X-ray system, together with the shock wave transducer, being arranged to be fixed with respect to the X,Y and Z axes and being pivotable about the focus.

In the case of an undertable or underpatient arrangement as mentioned above, the top of the treatment table has an opening for the X-rays and the ultrasonic waves to pass through. In such a case, the part of the body concerned in which the concretion or the tissue to be destroyed is situated is positioned in the region of the said opening.

However, it is also possible for the lithotripter according to the invention to be operated in a so-called overtable or overpatient arrangement. In this case the image intensifier of the X-ray system is situated below the patient, whereas the unit comprising the shock wave transducer, X-ray emitter and ultrasonic locating transducer is situated above the patient. This has advantages in, for example, therapy carried out to destroy concretions in the form of gall stones.

In this case there is of course no need for the top of the table to contain an opening, thus enabling the patient more comfortably to lie down. It will be appreciated that in this case the top of the treatment table should be composed of a material which is transparent to X-rays, such as perspex. Otherwise X-ray location would not be possible.

Finally, provision may be made for the X-ray system, together with the shock wave transducer, to be arranged on a frame as mentioned above, which frame is displaceable in the vertical direction by a drive which engages with a preferably vertical pillar, and is pivotable through an angle about the axis of the pillar and about its own pivot axis by the said drive. The divided angles of pivot mentioned above for X-ray location of the concretion or tissue will be small ones, such as ±15° from the rest position. If the large angle of pivot is 180°, the system can for example be converted from having the unit comprising shock wave transducer X-ray emitter and ultrasonic locating transducer in an undertable or underpatient arrangement to having it in an overtable or overpatient arrangement. After this the system can again be pivoted through small angles for locating purposes, such as ±15°.

BRIEF DESCRIPTION OF THE DRAWINGS

In order that the invention may be more readily understood some embodiments thereof will now be described, by way of example, with reference to the accompanying drawings, in which.

DESCRIPTION OF THE PREFERRED EMBODIMENTS

Figure 1:
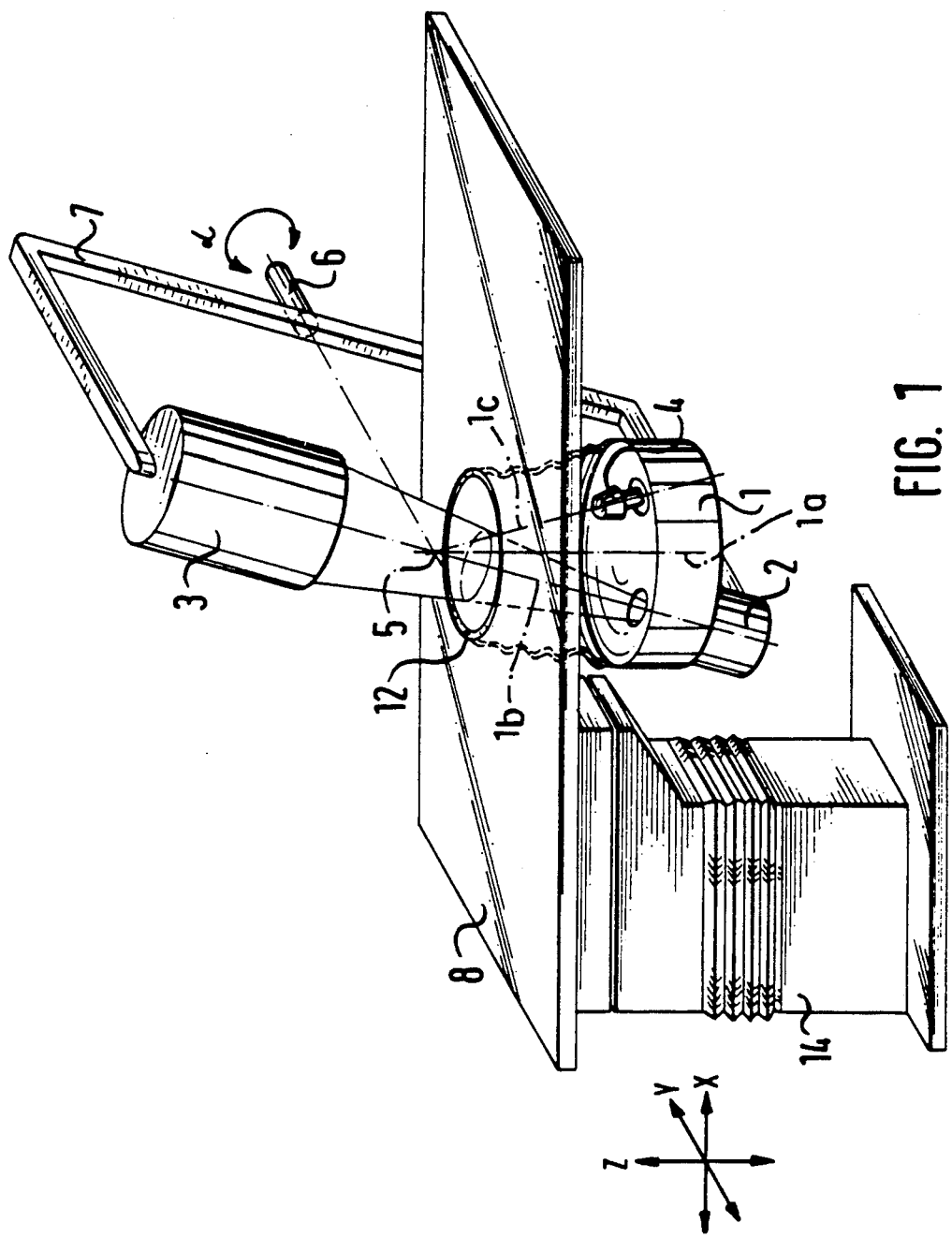
FIG. 1 is a schematic perspective view of a first embodiment of a lithotripter constructed in accordance with the invention and having a treatment table which can be moved along X,Y, and Z axes.

In the following description, the same reference characters are used to designate the same parts.

Figure 2:
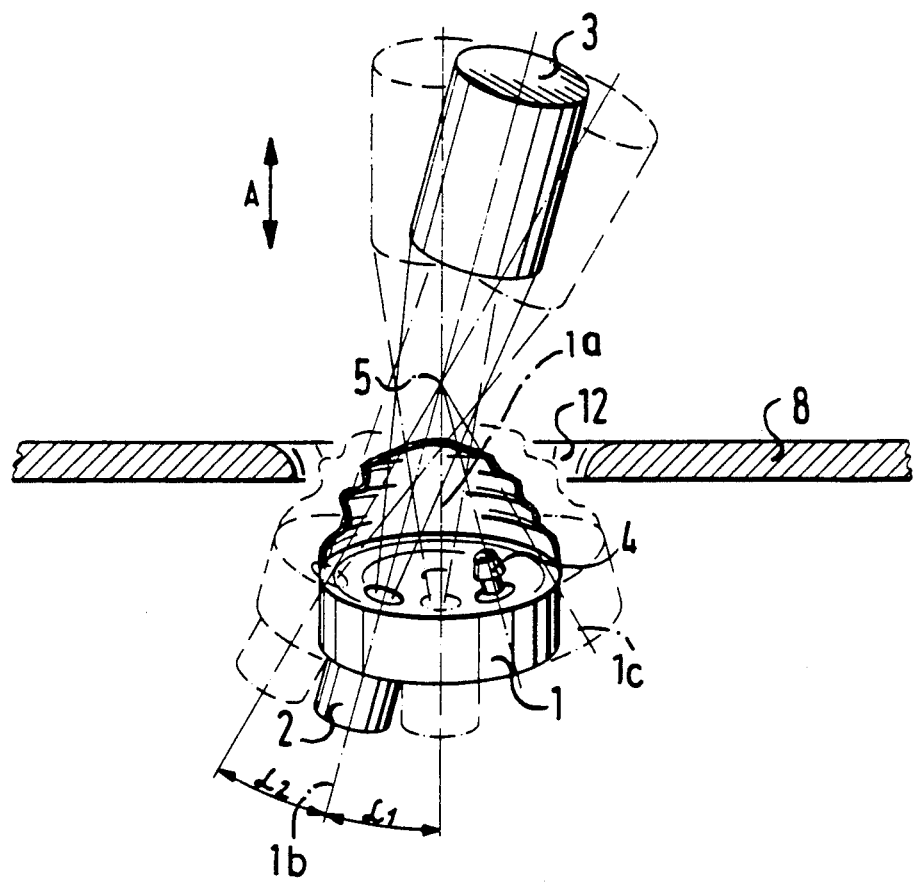
FIG. 2 is a schematic perspective view of a unit comprising an ultrasonic shock wave generating transducer, an X-ray emitter and an ultrasonic locating transducer disposed in an undertable arrangement and also an image intensifier forming part of the lithotripter of FIG. 1, with a pivoting movement for the purpose of X-ray location being indicated diagrammatically.

Referring to FIGS. 1 and 2 of the drawings, there is shown a lithotripter having a unit comprising an ultrasonic shock wave generating transducer 1, an X-ray emitter 2 and an ultrasonic locating transducer 4, which is described in greater detail below and which is arranged on one, free, limb of a U-shaped frame 7. Fixed to the other limb of the frame 7 is an image intensifier 3 which is disposed opposite the unit to receive X-ray emission from the X-ray emitter 2. The U-shaped frame 7 has a pivot axis 6 about which it can be pivoted through an angle α by a drive as will be explained below. The lithotripter has a treatment table comprising a top 8 and a supporting upright 14. A drive (not shown) housed in the upright 14 of the table allows the top 8 to be moved along X,Y and Z axes so that the focus of the shock wave transducer 1 can be positioned precisely on the concretion or tissue which is to be destroyed in the body of a patient lying on the table top 8.

In the top 8 is an opening 12 in which the part of the patient's body containing the concretion or tissue to be destroyed is placed.

As can be seen even from FIG. 1, the X-ray emitter 2 and the ultrasonic locating transducer 4 are arranged or mounted in the shock wave transducer 1 and are offset from the axis 1a of the shock wave transducer in such a way that the axis of the shock wave transducer 1, the axis 1b of the X-ray emitter 2 and the axis 1c of the ultrasonic locating transducer 4 intersect at the focus 5 of the shock wave transducer 1. In the embodiment shown, the focus 5 forms the isocenter for the pivoting movement of the X-ray system 2,3 and its frame 7. By the same token, an imaginary linear extension of the pivot axis 6 of the frame 7 intersects the focus in any pivoted position, as is indicated diagrammatically in FIG. 1.

In the lithotripter shown, the position of the ultrasonic locating transducer 4 is a mirror image of that of the X-ray emitter 2, about the axis of the shock wave transducer 1.

By pivoting the frame 7 through an angle α=180°, the shock wave transducer 1 and the parts connected to it can be changed from the undertable or underpatient arrangement shown to a so-called overtable or over patient arrangement. Even though the undertable arrangement allows the level of X-ray exposure to which the operating personnel are subject to be only small and will generally be the preferred arrangement, the overtable arrangement may be indicated for certain treatments.

The advantage of the offset arrangement of the X-ray emitter 2 in the shock wave transducer 1 will now be explained by particular reference to FIG. 2.

FIG. 2 shows the unit comprising shock wave transducer 1, X-ray emitter 2 and ultrasonic locating transducer 4 in an undertable arrangement below the table top 8 together with the image intensifier 3 which is positioned opposite the X-ray emitter 2, with the frame not being shown for reasons of clarity.

In the embodiment shown, the X-ray emitter 2 is offset in the spherical cup of the shock wave transducer 1 in such a way that the axis 1b of the X-ray emitter 2 and the axis 1c of the locating transducer 4 each lie at an angle of 15° with respect to the axis of the shock wave transducer 1. The axis of the ultrasonic locating transducer 4 is positioned as a mirror image of the X-ray emitter 2 and is diametrically opposed to it about the axis of the shock wave transducer 1.

As explained above, X-ray location of the concretion or tissue to be destroyed calls for the patient's body to be irradiated in two planes. This is normally done with a so-called AP projection in which the X-rays pass through the patient's body perpendicularly and with a projection rotated through 30° from the AP projection. For this to be achieved in the lithotripter according to the invention all that is needed for the AP projection is a pivoting movement of the unit about the pivot axis 6, through an angle α of 15° and for the 30° projection a pivoting movement through an angle of 15° in the other direction, each from a rest or datum position in which the axis of the shock wave transducer 1 is vertical. This gives as great a travel as possible in the direction of the double-headed arrow A in FIG. 2, along which the unit may possibly need to be moved in order to bring the focus into co-incidence with the concretion or tissue to be destroyed.

The advantage of the offset arrangement of the X-ray emitter in the shock wave transducer 1 can be clearly seen by considering the following: If for example the X-ray emitter were placed in the centre of the shock wave transducer 1, the travel of the unit towards the table top 8 would be greatly restricted by the fact that when performing a pivoting movement through a full 30° angle, the stock wave transducer 1 would strike against the underside of the table top 8.

Figure 3:
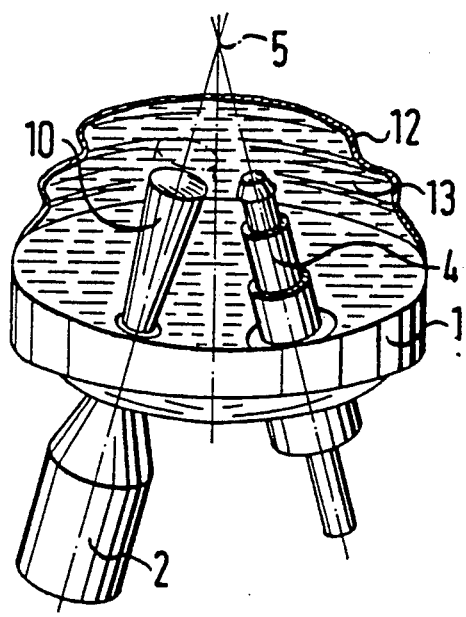
FIG. 3 is a schematic perspective view of another embodiment of a unit comprising a shock wave transducer, an X-ray emitter and ultrasonic locating transducer.

The FIG. 3 embodiment of a unit comprising the shock wave transducer 1, the X-ray emitter 2 and the ultrasonic locating transducer 4 differs from that of FIG. 1 in that the spherical cup of the transducer 1 is filled with a liquid such as water to act as a coupling medium 13 and is sealed or closed off from the external environment by a membrane 12.

Furthermore, projecting from the front end of the X-ray emitter 2 is a gas-filled tube 10 which is closed off from its surroundings. The cross-section of the tube 10 is matched to the cross-section of the cone of X-rays emitted by the X-ray emitter 2 for locating purposes. As the tube 10 is sealed with respect to the coupling medium 13 at all times, the attenuation of the X-rays in the coupling medium is reduced to improve X-ray location. The tube 10 can be displaced along the axis 1b of the X-ray emitter 2, as is diagrammatically illustrated by the dashed lines in FIG. 3.

Figure 4:
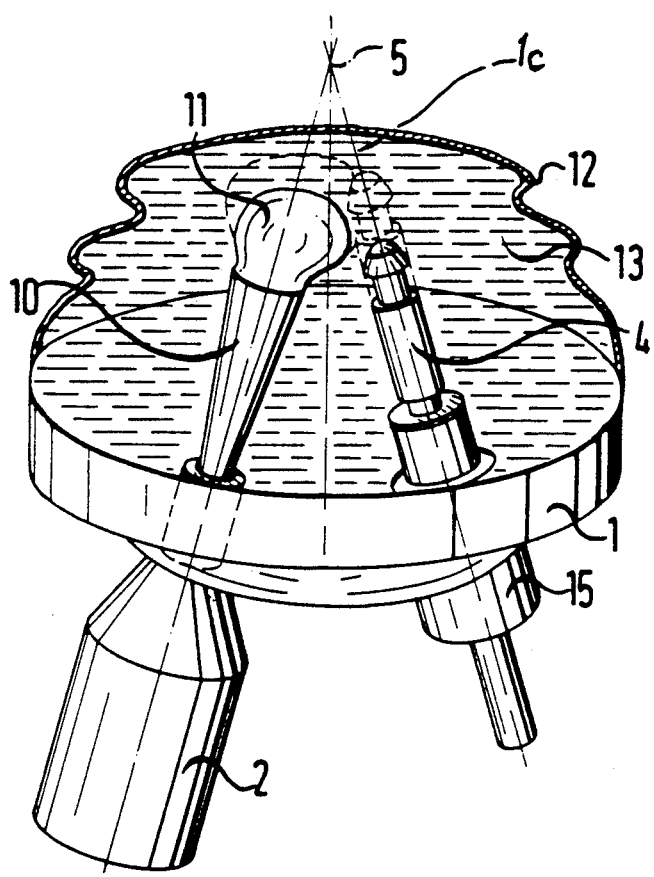
FIG. 4 is a schematic perspective view of yet another embodiment of a unit comprising a shock wave transducer, an X-ray emitter and ultrasonic locating transducer.

In the embodiment shown in FIG. 4, the end of the tube 10 adjacent the focus 5 is closed off with a balloon 11 which can be filled with, and evacuated of, gas by means of a pneumatic system (not shown). If for purposes of X-ray location the length of the path taken by the X-rays through the coupling medium 13 needs to be shortened even more, the balloon 11 is inflated with gas. The coupling medium 13 which is thereby displaced is collected in an equalising system (not shown) so that the pressure in the coupling medium filled space closed off by the membrane 12 will remain constant. To allow the application of the ultrasonic shock waves to be initiated, the balloon 11 is evacuated by the pneumatic system (not shown). At the same time the coupling medium 13 collected in the equalising system (not shown) is fed back again. This ensures that the shock wave transducer 1 is satisfactorily coupled to the patient's body during the therapy. The ultrasonic transducer 4 is connected to a scanner mechanism 15 which allows it to be moved along its longitudinal axis 1c as diagrammatically illustrated by the dashed lines in FIG. 4, as well as being rotated about this longitudinal axis.

Figure 5:
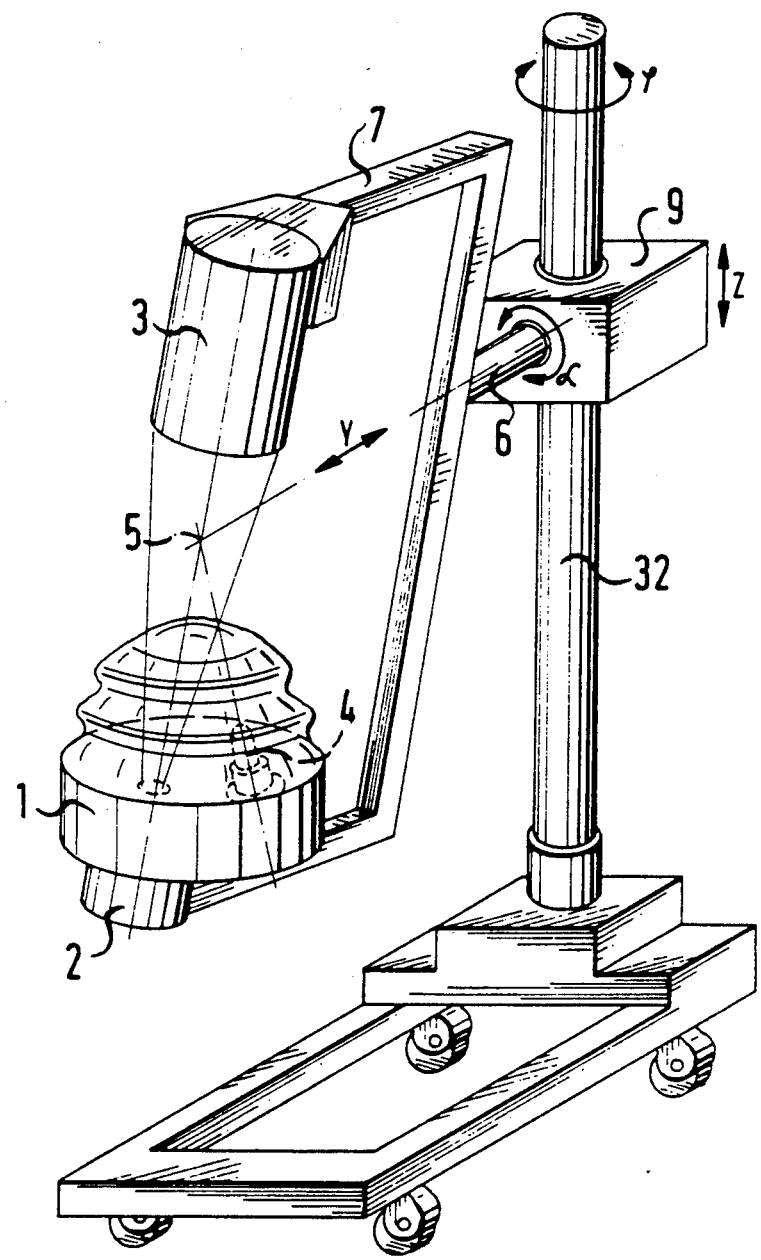
FIG. 5 is a schematic perspective view of another embodiment of lithotripter.

Referring now to FIG. 5, the frame 7 on which the unit comprising the shock wave transducer 1, X-ray emitter 2 and ultrasonic locating transducer 4, and the image intensifier 3, are arranged can be moved in the vertical direction along a Z axis, via the pivot shaft 6, by a drive 9 which engages with a vertical pillar 32. The axis of the pillar is the Z axis. The drive 9 also allows movement to be performed in the direction of the Y axis and pivoting movement to be performed through an angle ρ about the axis of the pillar 32 as well as a pivoting movement through an angle α about the axis of pivot 6 of the frame 7.

The drive further permits not only pivoting movements through small angles α, such as through ±15° for example, for locating purposes, but also pivoting movements through large angles, such as through 180° to allow the lithotripter to be changed over from undertable to overtable use, i.e. underpatient to overpatient use.

Figure 6:
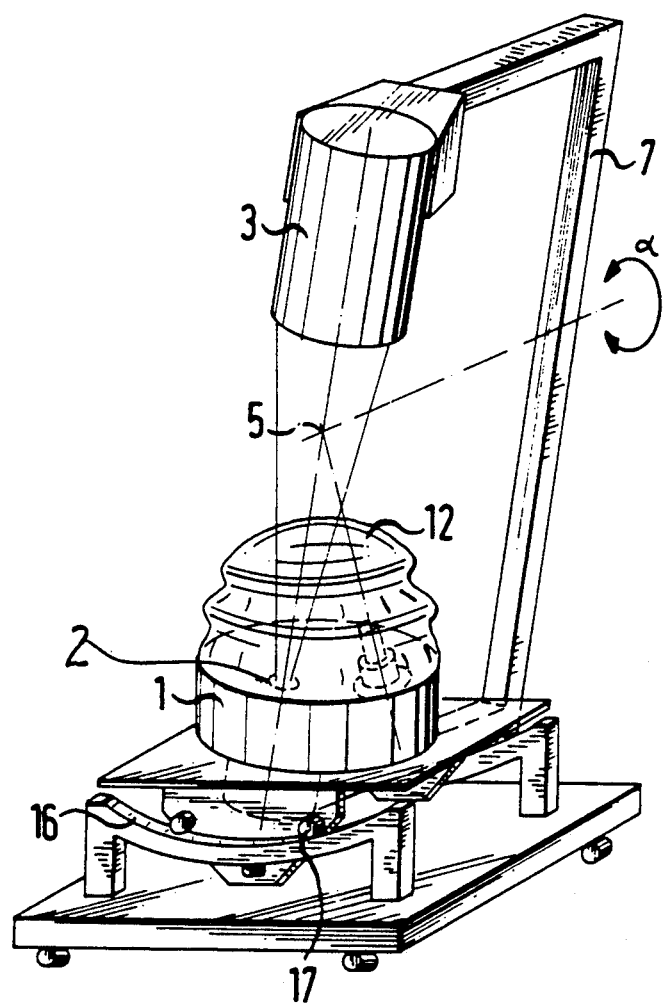
FIG. 6 is a schematic perspective view of a further embodiment of lithotripter.

Finally, in the embodiment of lithotripter, shown in FIG. 6, the unit comprising shock wave transducer 1, X-ray emitter 2 and ultrasonic locating transducer 4 is arranged to pivot co-focally about the focus 5, which therefore does not move, in unison with the image intensifier 3, on an arcuate guide 16 through an angle α (in both directions). Rollers 17 or the like suitably connected to the system roll on or against the guide 16 to allow a pivoting movement through the angle α, which may for example be ±15°, to be performed for locating purposes.

It should be appreciated that the invention is not limited to the embodiment herein described but includes all modifications and variations falling within the scope of the invention. For example, instead of either of the X-ray emitter 2 and ultrasonic locating transducer 4 being offset, the x-ray emitter 2 or locating transducer 4 may be disposed along the axis of the shock wave transducer 1.

We claim:

1. A lithotripter for destroying concretions or tissues by means of focussed ultrasonic shock waves comprising:
   (a) a transducer for generating focussed ultrasonic shock waves, said transducer having an axis and a focus on said axis;
   (b) at least one X-ray imaging system for locating a concretion or tissue to be destroyed, said system including an X-ray emitter having an axis and an image intensifier spaced from said emitter and positioned to receive X-ray emissions therefrom, said emitter and intensifier being arranged on a frame which is pivotable about an axis for location of concretions or tissues in various image planes,
   (c) at least one ultrasonic locating transducer having an axis,
   (d) means for mounting said at least one X-ray emitter and said at least one ultrasonic locating transducer in said ultrasonic shock wave generating transducer, said emitter and said locating transducer being offset from the axis of the shock wave transducer, and the axes of the shock wave transducer, X-ray emitter and locating transducer all intersecting at the focus of the shock wave transducer, and
   (e) means for positioning the focus on a concrement or tissue to be destroyed.

2. A lithotripter as claimed in claim 1, wherein the focus of the ultrasonic shock wave generating transducer constitutes an isocenter, for the pivoting movement of the X-ray system and of said frame and wherein an imaginary linear extension of said pivoting axis intersects the focus in any pivoted position of said X-ray system and said frame.

3. A lithotripter as claimed in claim 1, wherein the ultrasonic locating transducer occupies a mirror image position with respect to that of the X-ray emitter, about the axis of the ultrasonic shock wave generating transducer.

4. A lithotripter as claimed in claim 1, wherein, the X-ray emitter is provided with a gas-filled tube which is closed off with respect to any ambient medium and which has a cross-section which is at least equal to that of an X-ray beam emitted by the X-ray emitter for locating purposes.

5. A lithotripter as claimed in claim 4, wherein the gas filled tube has a free end adjacent said focus and a gas fillable balloon closes off the free end of the tube.

6. A lithotripter as claimed in claim 1, and comprising a treatment table for supporting a patient to be treated, said treatment table being displaceable along X, Y and Z axes to position said focus on the concretion or tissue to be destroyed, wherein the ultrasonic shock wave generating transducer together with the X-ray emitter and ultrasonic locating transducer and the image intensifier are fixed with respect to the movement of the treatment table along said X, Y and Z axes and are pivotable about said focus.

7. A lithotripter as claimed in claim 1, wherein the ultrasonic shock wave generating transducer together with the X-ray emitter and ultrasonic locating transducer and the image intensifier are mounted on a frame which cooperates with an arcuate guide to permit pivoting movements of the frame about said focus and such that said focus does not move during said pivoting movements.

8. A lithotripter according to claim 1 wherein the locating transducer and the X-ray emitter are each offset from the axis of the shock wave transducer by about 15°.

9. A lithotripter according to claim 1 wherein the axes of the locating transducer and the X-ray emitter intersect at an angle of about 30°.

10. A lithotripter as claimed in claim 1 wherein the ultrasonic shock wave generating transducer, together with the X-ray emitter and the ultrasonic locating transducer, and the image intensifier are mounted on a frame which is supported on a pillar having an axis, and further comprising drive means engaging said pillar for moving the frame along Y and Z axes, with the Z axis being the axis of the pillar and the Y axis extending perpendicular to the pillar and toward the focus, and for pivoting said frame about a pivot axis through relatively small angles for locating purposes and through relatively large angles to enable the lithotripter to be changed from underpatient to overpatient use.

11. A lithotripter or destroying concretions or tissues by means of focussed ultrasonic shock waves comprising:
   (a) a transducer for generating focussed ultrasonic shock waves, said transducer having an axis and a focus on said axis;
   (b) at least one X-ray imaging system for locating a concretion or tissue to be destroyed by said shock waves at said focus, said system including an X-ray emitter having an axis and an image intensifier spaced from said X-ray emitter and positioned to receive X-ray emissions therefrom;
   (c) at least one ultrasonic locating transducer having an axis, said X-ray emitter and said ultrasonic locating transducer being mounted on said ultrasonic shock wave generating transducer and oriented relative to each other such that their respective axes intersect at said focus; and
   (d) said X-ray emitter being provided with a gas-filled tube which is closed off with respect to any ambient medium and which has a cross-section which is at least equal to that of an X-ray beam emitted by the X-ray emitter for locating purposes.

12. A lithotripter according to claim 11 wherein the gas-filled tube has a free end adjacent said focus and a gas-fillable balloon closes off the free end of the tube.

* * * * *